United States Patent
Tsukabayashi et al.

(10) Patent No.: US 8,713,990 B2
(45) Date of Patent: May 6, 2014

(54) GAS SENSOR

(75) Inventors: Shunji Tsukabayashi, Saitama (JP);
Hidetoshi Oishi, Saitama (JP);
Kazuhiro Okajima, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 190 days.

(21) Appl. No.: 13/474,867

(22) Filed: May 18, 2012

(65) Prior Publication Data

US 2012/0291522 A1 Nov. 22, 2012

(30) Foreign Application Priority Data

May 20, 2011 (JP) ................................. 2011-114213

(51) Int. Cl.
*G01N 25/18* (2006.01)

(52) U.S. Cl.
USPC ........................................ 73/25.05; 73/25.03

(58) Field of Classification Search
USPC ............ 73/23.2, 23.21, 25.03, 25.05; 422/94, 422/95, 98
See application file for complete search history.

(56) References Cited

U.S. PATENT DOCUMENTS

| | | | | |
|---|---|---|---|---|
| 4,443,791 A * | 4/1984 | Risgin et al. | ................... | 340/634 |
| 5,831,146 A | 11/1998 | Newman | | |
| 7,028,530 B2 * | 4/2006 | Katsuki et al. | ............... | 73/25.03 |
| 7,827,847 B2 * | 11/2010 | Oishi et al. | ...................... | 73/23.2 |
| 7,963,145 B2 * | 6/2011 | Hamatani et al. | ............ | 73/23.31 |
| 8,109,130 B2 * | 2/2012 | Dimeo et al. | ................. | 73/31.05 |
| 2008/0175759 A1 * | 7/2008 | Oishi et al. | ...................... | 422/98 |
| 2011/0023580 A1 * | 2/2011 | Oishi et al. | ...................... | 73/23.2 |
| 2011/0158854 A1 * | 6/2011 | Yamagishi et al. | ............. | 422/83 |

FOREIGN PATENT DOCUMENTS

| | | |
|---|---|---|
| DE | 69808553 T2 | 2/2003 |
| JP | 2004-251862 A | 9/2004 |
| JP | 2006153598 A | 6/2006 |
| JP | 2006349513 A | 12/2006 |
| JP | 2008139165 A | 6/2008 |
| JP | 2008175711 A | 7/2008 |
| JP | 2010230385 A | 10/2010 |

OTHER PUBLICATIONS

German Search Report file No. 10 2012 208.384.7 dated Sep. 14, 2012.
JP Office Action for JP Application No. 2011-114213 dated Apr. 16, 2013.

* cited by examiner

*Primary Examiner* — Lisa Caputo
*Assistant Examiner* — Punam Roy
(74) *Attorney, Agent, or Firm* — Squire Sanders (US) LLP

(57) ABSTRACT

A simple gas sensor for detecting a concentration of a detected gas with high accuracy, in which a thermal interference can hardly occur between a normal detection element pair and a reference detection element pair, is provided.

7 Claims, 12 Drawing Sheets

<FIRST BRIDGE CIRCUIT (HYDROGEN CONCENTRATION:0)>

GAS SENSOR

CROSS REFERENCE TO RELATED APPLICATION

This application claims the priority of Japanese Application No. 2011-114213, filed on May 20, 2011, the entire specification, claims and drawings of which are incorporated herewith by reference.

BACKGROUND OF THE INVENTION

1. Field of the Invention

The present invention relates to a gas sensor.

2. Description of the Related Art

In recent years, a fuel cell which attracts attention as a power source of a fuel cell vehicle, etc., exhausts hydrogen (a detected gas) unconsumed in power generation from an anode. This hydrogen is diluted with a cathode off gas (a dilution gas) from a cathode of the fuel cell, and is exhausted to an exterior (an outside) of the vehicle.

A hydrogen concentration of the gas (a diluted gas) exhausted to the external of the vehicle in the above described manner is detected by a catalytic combustion type hydrogen sensor (a gas sensor) (see JP 2004-251862 A). Also, since a detection element to catalytically combust the hydrogen deteriorates with the use of the hydrogen sensor, the hydrogen sensor is provided with a normal detection element pair and a reference detection element pair.

In particular, the normal detection element pair is provides with a first detection element whose temperature is raised and whose resistor value is changed by contact with the hydrogen, and a first compensation element (a temperature-compensated element) which is inactive to the hydrogen. The reference detection element pair is provided with a second detection element whose temperature is raised and whose resistor value is changed by contact with the hydrogen and a second compensation element which is inactive to the hydrogen. Also, (1) at the time of normal operation, the reference detection element pair is not energized, but the normal detection element pair is energized and activated so as to detect a hydrogen concentration, and (2) at the time when deterioration of the normal detection element pair is determined, the reference detection element pair is energized and activated, an output of the normal detection element pair is compared to an output of the reference detection element pair so as to determine whether the normal detection element pair deteriorates or not.

However, since the hydrogen sensor disclosed in JP 2004-251862 A is provided with a first element housing which houses the normal detection element pair and a second element housing which houses the reference detection element pair, the hydrogen sensor can not be minimized. Also, when a plurality of element housings are provided, a heater for heating a detection chamber in the element housing and a temperature sensor for detecting a temperature in the detection chamber are required for every element housing. As a result, the number of parts is increased, and the cost for manufacturing the hydrogen sensor is increased.

For this reason, as disclosed in JP 2004-251862 A, the normal detection element pair and the reference detection element pair can be placed in one element housing. However, a thermal interference may occur between the normal detection element pair and the reference detection element pair. As a result, a detection accuracy of the hydrogen concentration may be lowered.

Therefore, an object of the present invention is to provide a simple gas sensor for detecting a concentration of a detected gas with high accuracy.

SUMMARY OF THE INVENTION

In order to achieve the above object, the present invention provides a gas sensor, comprising: a normal detection element pair which has a first detection element whose temperature is raised and whose resistor value is changed by contact with a detected gas and a first compensation element which is inactive to the detected gas, and outputs a first signal corresponding to a concentration of the detected gas based on a difference between the resistor value of the first detection element and a resistor value of the first compensation element; a reference detection element pair which has a second detection element whose temperature is raised and whose resistor value is changed by contact with the detected gas and a second compensation element which is inactive to the detected gas, and outputs a second signal which is used as a deterioration standard corresponding to the concentration of the detected gas based on a difference between a resistor value of the second detection element and a resistor value of the second compensation element at the time when deterioration of the normal detection element pair is determined; and an element housing which has a detection chamber which houses both of the normal detection element pair and the reference detection element pair, wherein a first arrangement direction of the first detection element and the first compensation element is parallel to a second arrangement direction of the second detection element and the second compensation element, the normal detection element pair and the reference detection element pair are placed in a direction which is perpendicular to the first arrangement direction and the second arrangement direction, and a first sequential order of the first detection element and the first compensation element is reverse to a second sequential order of the second detection element and the second compensation element.

According to the above structure, the gas sensor has a simple structure which is provided with one element housing. Therefore, the gas sensor can be minimized easily. Also, the gas sensor is provided with one element housing, and the element housing is provided with one detection chamber. Therefore, if the gas sensor is provided with a heater for heating the detection chamber and a temperature sensor for detecting a temperature in the detection chamber, only one heater and only one temperature sensor are provided. For this reason, the number of parts is not increased significantly, and the cost for manufacturing the gas sensor is reduced.

Also, since the first arrangement direction of the first detection element and the first compensation element is parallel to the second arrangement direction of the second detection element and the second compensation element, the normal detection element pair and the reference detection element pair are placed in the direction which is perpendicular to the first arrangement direction and the second arrangement direction, and the first sequential order of the first detection element and the first compensation element is reverse to the second sequential order of the second detection element and the second compensation element, the first detection element and the second detection element whose temperatures are increased (heat generation) in contact with the detected gas in the detection chamber are placed separated from each other.

For this reason, the thermal interference can hardly occur between the first detection element and the second detection element. That is, it becomes difficult to change the temperature and the resistor value of the first detection element by the heat from the second detection element, and it becomes difficult to change the temperature and the resistor value of the second detection element by the heat from the first detection element. Accordingly, the first signal of the normal detection element pair and the second signal of the reference detection element pair can be changed easily in response to only concentration of the detected gas. Therefore, the concentration of the detected gas can be detected with high accuracy. Also, the deterioration of the normal detection element pair can be preferably determined.

Also, the gas sensor is preferably provided with a heater for heating the detection chamber.

According to the above structure, in addition to the detection chamber, the normal detection element pair (the first detection element, and the first compensation element) and the reference detection element pair (the second detection element, and the second compensation element) can be heated (warmed up) by only one heater. Also, since the number of the parts of the heater is minimized, and the cost for manufacturing the gas sensor is reduced.

Further, since an atmospheric temperature of the normal detection element pair becomes equal to an atmospheric temperature of the reference detection element pair easily, the deterioration of the normal detection element pair can be determined with high accuracy.

Also, the gas sensor is preferably provided with a temperature sensor which is placed in the detection chamber and is used for detecting a temperature in the detection chamber; and a correction unit for correcting the first signal of the normal detection element pair and the second signal of the reference detection element pair based on the temperature in the detection chamber detected by the temperature sensor respectively, wherein the first detection element, the first compensation element, the second detection element, and the second compensation element are preferably placed around the temperature sensor.

According to the above structure, since the first detection element, the first compensation element, the second detection element, and the second compensation element are placed around the temperature sensor, the element housing (the detection chamber) is minimized, and the temperature detected by the temperature sensor becomes equal to the atmospheric temperature of the normal detection element pair and the reference detection element pair easily.

Also, in this way, since the temperature detected by the temperature sensor becomes equal to the atmospheric temperatures of the normal detection element pair and the reference detection element pair easily, the correction unit can preferably corrects the first signal of the normal detection element pair and the second signal of the reference detection element pair based on the temperature detected by the temperature sensor respectively. Therefore, the concentration of the detected gas can be detected with high accuracy, and the deterioration of the normal detection element pair can be preferably determined.

Also, the gas sensor is preferably provided with an insulating member which reduces the thermal interference between at least two elements of the first detection element, the first compensation element, the second detection element, and the second compensation element.

According to the above structure, the insulating member reduces the thermal interference between at least two elements.

Also, in the gas sensor, the insulating member is preferably cross-shaped so as to reduce the thermal interference among the first detection element, the first compensation element, the second detection element, and the second compensation element.

According to the above structure, the cross-shaped insulating member can reduce the thermal interference among the first detection element, the first compensation element, the second detection element, and the second compensation element.

Also, in the gas sensor, the insulating member is cylindrical, and the cylindrical insulating members are provided around the first detection element and the second detection element respectively.

According to the above structure, the cylindrical insulating members can reduce the thermal interference between the first detection element and the second detection element respectively.

Also, in the gas sensor, a through hole through which the detected gas passes is formed on a side wall of the cylindrical insulating member.

According to the above structure, the detected gas can be let in and out of the cylindrical insulating member via the through hole.

DETAILED DESCRIPTION OF THE PREFERRED EMBODIMENTS

<<First Embodiment>>

Figure 1:
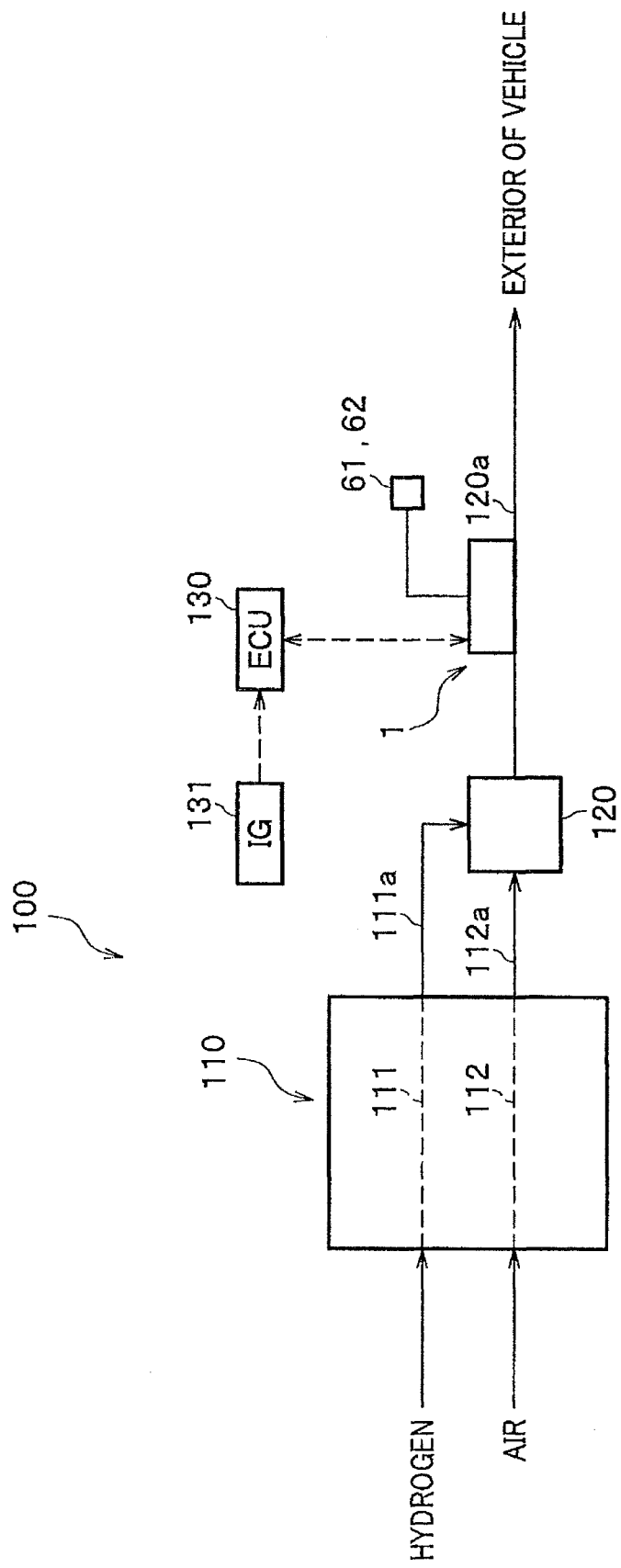
FIG. 1 is a block diagram of a fuel cell system according to a first embodiment.

Hereinafter, with reference to FIGS. 1-8, a first embodiment of the present invention will be explained.

First, a fuel cell system 100 into which a hydrogen sensor 1 (a gas sensor) is integrated will be explained. The fuel cell system 100 is mounted on a fuel cell vehicle (a mobile unit), and is provided with a fuel cell stack 110 (a fuel cell), a dilutor 120, a hydrogen sensor 1, and an ECU 130 (Electronic Control Unit).

<Fuel Cell Stack>

The fuel cell stack 110 is a Polymer Electrolyte Fuel Cell (PEFC), and is composed by stacking a plurality of single cells, each of which is made by sandwiching a Membrane Electrode Assembly (MEA) with separators (not shown). The MEA is provided with an electrolyte membrane (a solid polymer membrane), and an anode and a cathode for sandwiching the electrolyte membrane. A channel and a through hole which serve as an anode flow path 111 and a cathode flow path 112 are formed on each separator.

Also, when the hydrogen is supplied from a hydrogen tank (not shown) to the anode via the anode flow path 111 and air containing oxygen is supplied from a compressor (not shown) which takes in outside air to the cathode via the cathode flow path 112, an electrode reaction is caused by a catalyst (PT, etc.) contained in the anode and the cathode and the fuel cell stack 110 is moved to a power generating condition. When the fuel cell stack 110 in the power generating condition is connected to an outer load (e.g., a motor for traveling) so as to extract a current, the fuel cell stack 110 starts power generation.

Also, an anode off gas containing an unconsumed hydrogen exhausted from the anode flow path 111 is supplied to the dilutor 120 through a pipe 111a. On the other hand, a cathode off gas (a dilution gas) exhausted from the cathode flow path 112 is supplied to the dilutor 120 through a pipe 112a.

<Dilutor>

The dilutor 120 is a vessel for diluting the hydrogen contained in the anode off gas with the cathode off gas, etc., and has a diluting space within it. Also, the diluted gas containing the hydrogen is exhausted to an exterior (an outside) of the vehicle through a pipe 120a.

<ECU>

The ECU 130 includes a CPU, a ROM, a RAM, a variety of interfaces, and an electronic circuit, etc. Also, when an ON signal of an IG 131 is detected, the ECU 130 hydrogen sensor 1 outputs a starting command. In addition, the IG 131 is a starting switch of the fuel cell system 100 (the fuel cell vehicle), and is placed around a driver's seat.

<<Structure of Hydrogen Sensor>>

Figure 2:
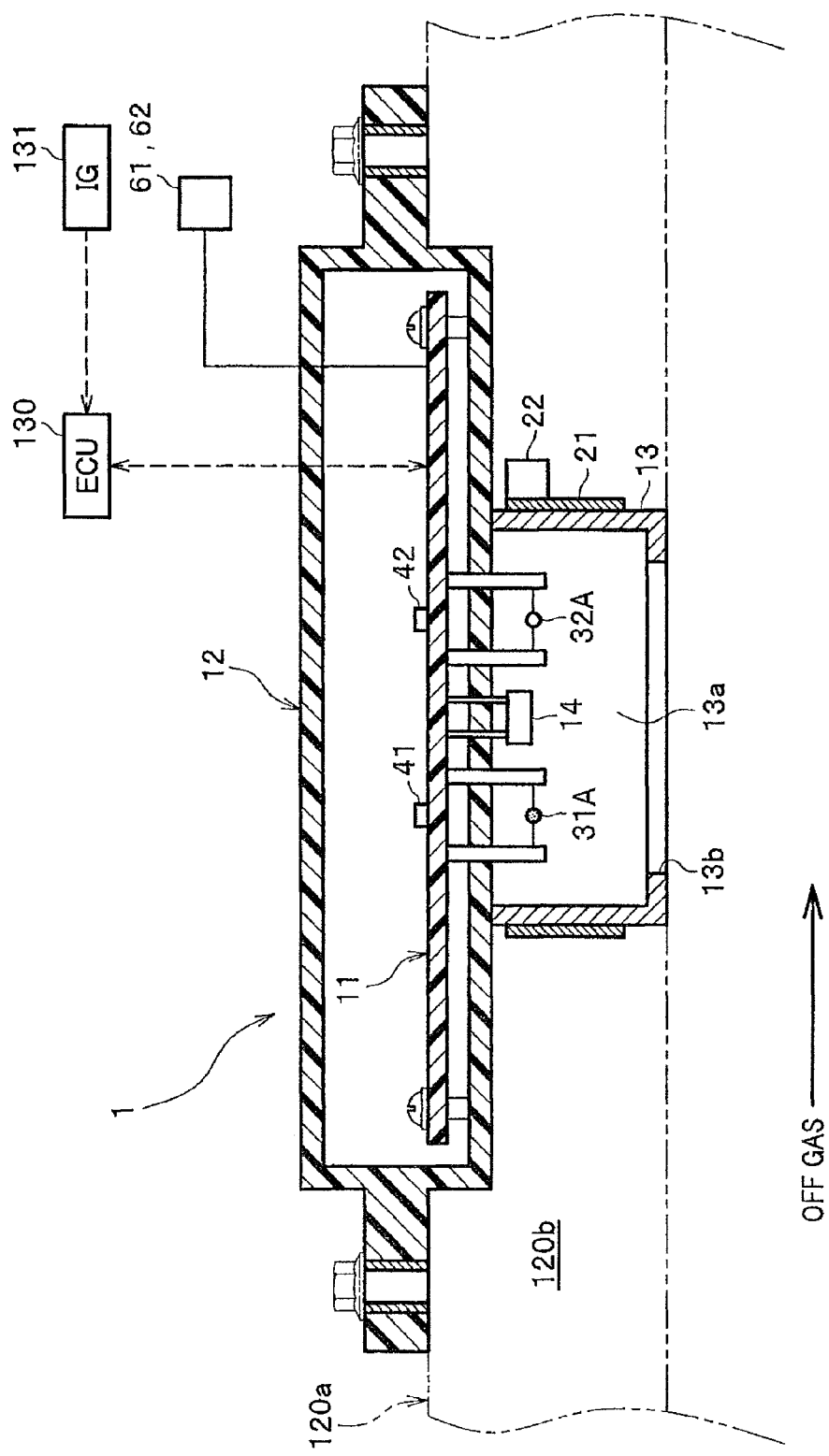
FIG. 2 is a vertical sectional view of a hydrogen sensor according to the first embodiment.

As shown in FIG. 2, the hydrogen sensor 1 is a catalytic combustion type for detecting the hydrogen concentration of the gas passing through the pipe 120a by causing a combustion of the hydrogen with the first detection element 31A.

The hydrogen sensor 1 is provided with a substrate 11 on which a predetermined circuit is formed, a slim-line casing 12 for housing the substrate 11, a cylindrical element housing 13 extending vertically downward from a bottom of the casing 12, a temperature sensor 14 for detecting a temperature in a detection chamber 13a, a cylindrical heater 21 attached to an outside of the element housing 13, and a temperature sensor 22 for detecting a temperature of the heater 21.

However, the shape of the element housing 13 is not limited to the cylindrical-shape, a polygonal-tube shape (e.g., a hexagonal-tube shape) may be used. Also, the shape, the position, and the number of the heater 21 are not limited to the above. For example, a plurality of plate-shaped heaters may be provided in the detection chamber 13a of the element housing 13.

The casing 12 is made of a resin such as a polyphenylene sulfide, etc. Also, the casing 12 is attached to an upper wall 120b of the pipe 120a via bolts.

<Element Housing>

The element housing 13 has the detection chamber 13a which lets in a gas containing hydrogen in order to detect the hydrogen. Also, a normal detection element pair P1 (a pair of the first detection element 31A and a first compensation element 32A) and a reference detection element pair P2 (a pair of a second detection element 31B and a second compensation element 32B) are placed in the detection chamber 13a (see FIG. 4). That is, the element housing 13 houses both of the normal detection element pair P1 and the reference detection element pair P2.

The element housing 13 is made of a material whose heat conductivity is high (e.g., a metal such as SUS, or a resin whose heat conductivity is high) in order to conduct heat of the heater 21 to the detection chamber 13a.

Also, a gas gateway 13b whose shape is circular in the horizontal plane if formed through a bottom wall of the element housing 13. Also, the gas containing the hydrogen is interchanged between the detection chamber 13a and the pipe 120a via the gas gateway 13b.

In addition, an explosion-proof filter (not shown) and a water-repellent filter (not shown) are provided so as to cover the gas gateway 13b. The explosion-proof filter ensures an explosion-proof character, and is made of a metal mesh or a porous body, etc. The water-repellent filter allows the gas (the hydrogen) to pass but does not allows a liquid (a water-drop) to pass, and are made of a tetrafluoroethylene membrane, etc.

<Temperature Sensor for Detection Chamber>

Figure 4:
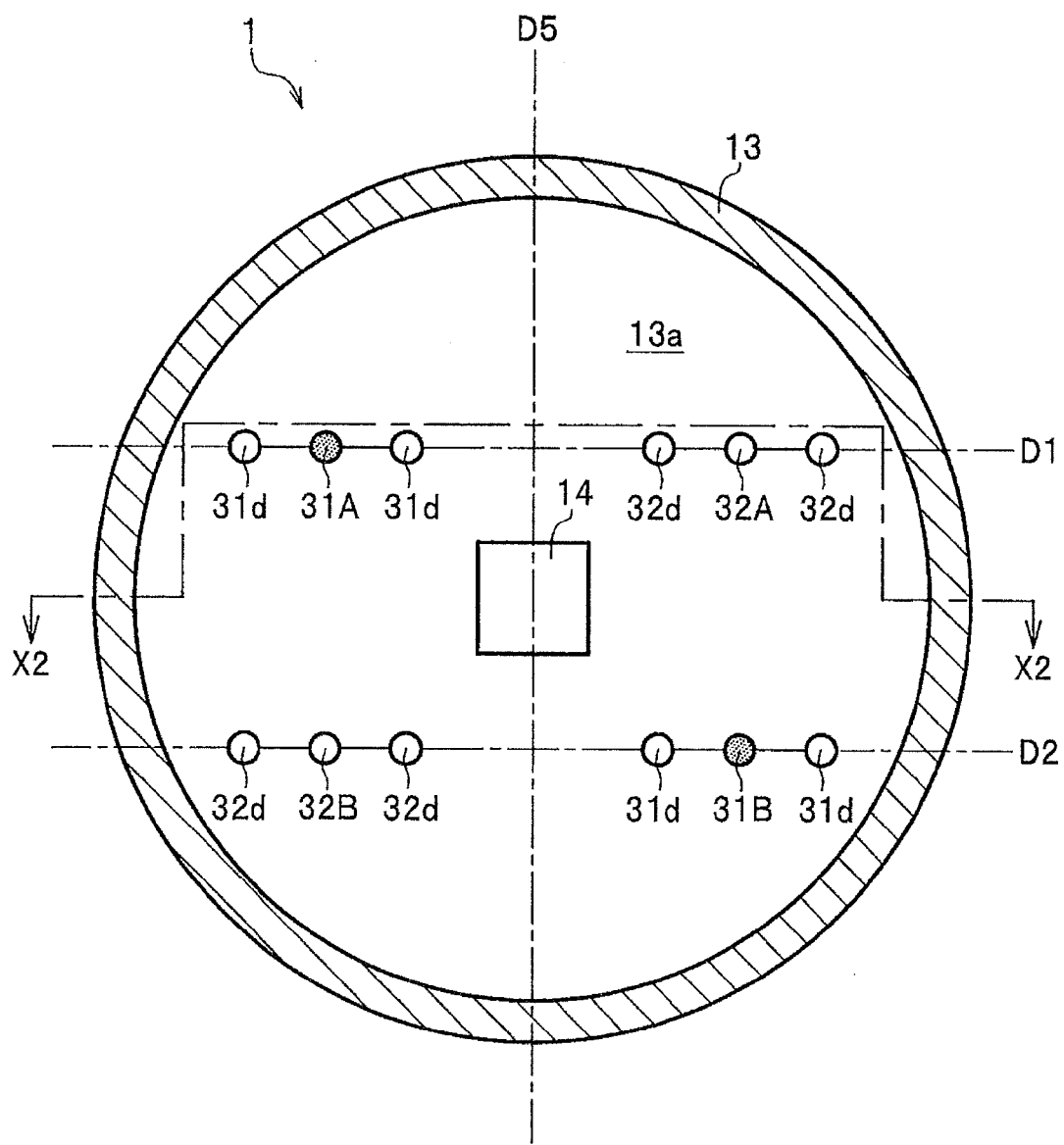
FIG. 4 is a horizontal sectional view of the hydrogen sensor according to the first embodiment taken along the line X1-X1 of FIG. 3.

The temperature sensor 14 is placed at the center of the detection chamber 13a whose shape is circular in the horizontal plane (i.e., on a center line of the cylindrical element housing 13) (see FIG. 4). Also, the temperature sensor 14 detects a temperature of the detection chamber 13a, and outputs the temperature signal to a microcomputer 51 described later (see FIG. 5).

Also, the first detection element 31A, the first compensation element 32A, the second detection element 31B, and the second compensation element 32B are placed around the temperature sensor 14 in the horizontal plane. In particular, the temperature sensor 14 is placed at the center of a virtual rectangle (i.e., at an intersection point of diagonal lines) where the first detection element 31A, the first compensation element 32A, the second detection element 31B, and the second compensation element 32B are placed at four apexes (four corners) of the virtual rectangle.

For this reason, the temperature of the detection chamber 13a detected by the temperature sensor 14 is approximately equal to atmospheric temperatures of the first detection element 31A, the first compensation element 32A, the second detection element 31B, and the second compensation element 32B. That is, since only one temperature sensor 14 can detect the atmospheric temperatures of four elements (i.e., the first detection element 31A, etc.), the number of the temperature sensor 14 can be reduced.

<Heater>

The heater 21 is an electric heater composed of a resistor, and is energized by a heater driving circuit 52 described later so as to generate heat. The heater 21 has a large temperature resistance coefficient (a resistance temperature coefficient), and is made of a material whose resistor value is linear to the temperature thereof. Examples of materials having such properties are metals such as platinum (Pt), molybdenum (Mo), tantalum (Ta), copper (Cu), etc., and alloys such as Nichrome, and SUS, etc.

Temperature Sensor for Heater

Figure 5:
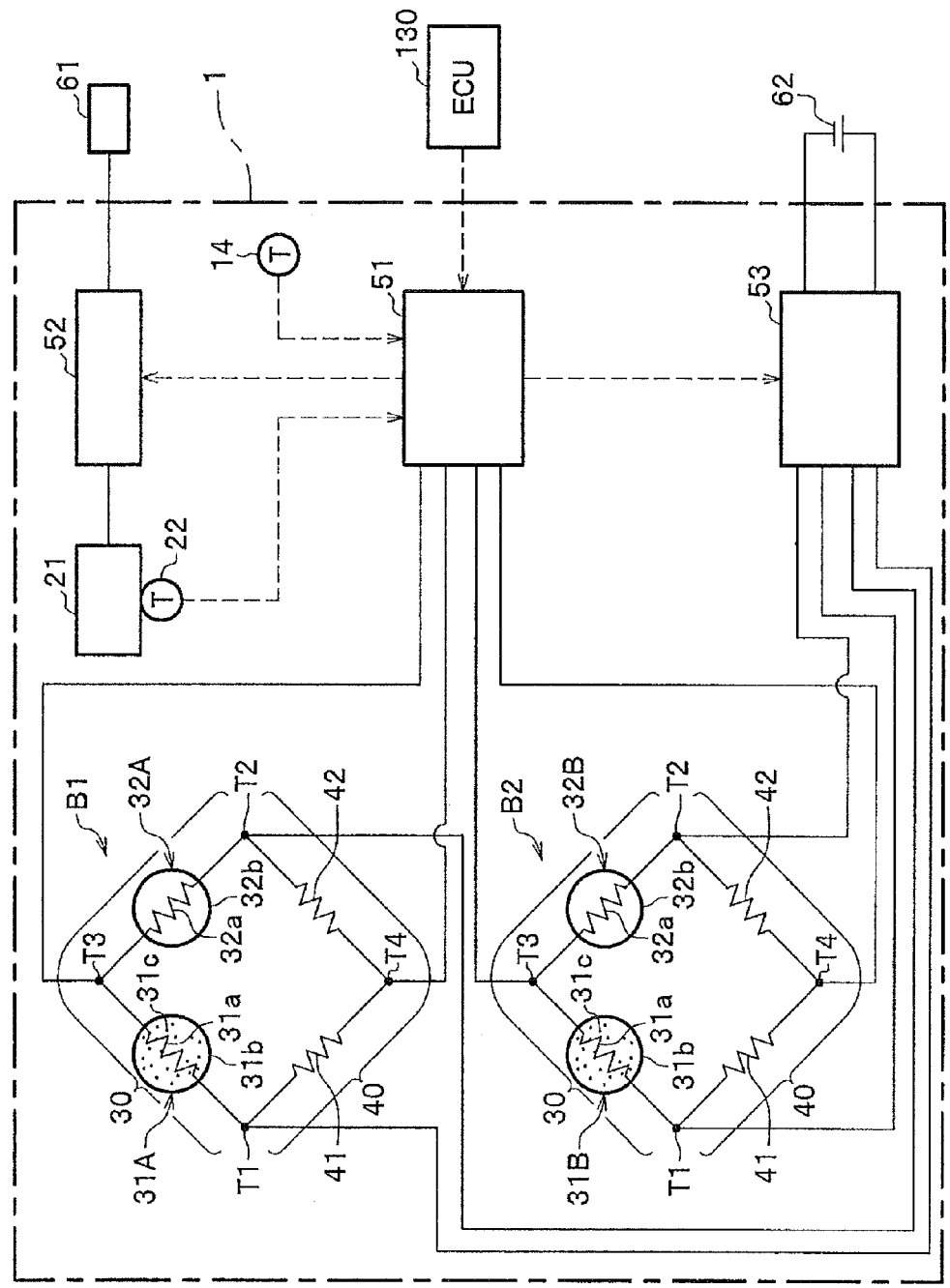
FIG. 5 is a circuit diagram of the hydrogen sensor according to the first embodiment.

The temperature sensor 22 detects the temperature of the heater 21, and outputs a temperature signal to the microcomputer 51 (see FIG. 5).

Bridge Circuit

As shown in FIG. 5, the hydrogen sensor 1 is provided with a first bridge circuit B1 including the normal detection element pair P1 (see FIG. 4) and a second bridge circuit B2 including the reference detection element pair P2.

The first bridge circuit B1 is a circuit which is energized at the time of normal operation so as to detect the hydrogen concentration. On the other hand, the second bridge circuit B2 is a circuit which is energized at the time when deterioration of the normal detection element pair P1 (the first bridge circuit B1) is determined in accordance with an instruction from the microcomputer 51 so as to detect the hydrogen concentration.

That is, a voltage is applied from the voltage generation circuit 53 described later to the first bridge circuit B1 in accordance of the instruction from the microcomputer 51 at the time of normal operation. On the other hand, a voltage is applied from the voltage generation circuit 53 to the first bridge circuit B1 and the second bridge circuit B2 in accordance the instruction from the microcomputer 51 at the time when deterioration of the normal detection element pair P1 (the first bridge circuit B1) is determined.

Here, since the structure of the first bridge circuit B1 is the same as that of the second bridge circuit B2, only the first bridge circuit B1 will be explained in detail hereinafter.

The first bridge circuit B1 is provided with a first serial side 30 and a second serial side 40.

First Bridge Circuit—First Serial Side

The first serial side 30 is provided with the first detection element 31A (resistor value $R_{31}$) and the first compensation element 32A (resistor value $R_{32}$), and the first detection element 31A is connected to the first compensation element 32A in series. Also, the normal detection element pair P1 is composed of a pair of the first detection element 31A and the first compensation element 32A (see FIGS. 3 and 4).

Figure 3:
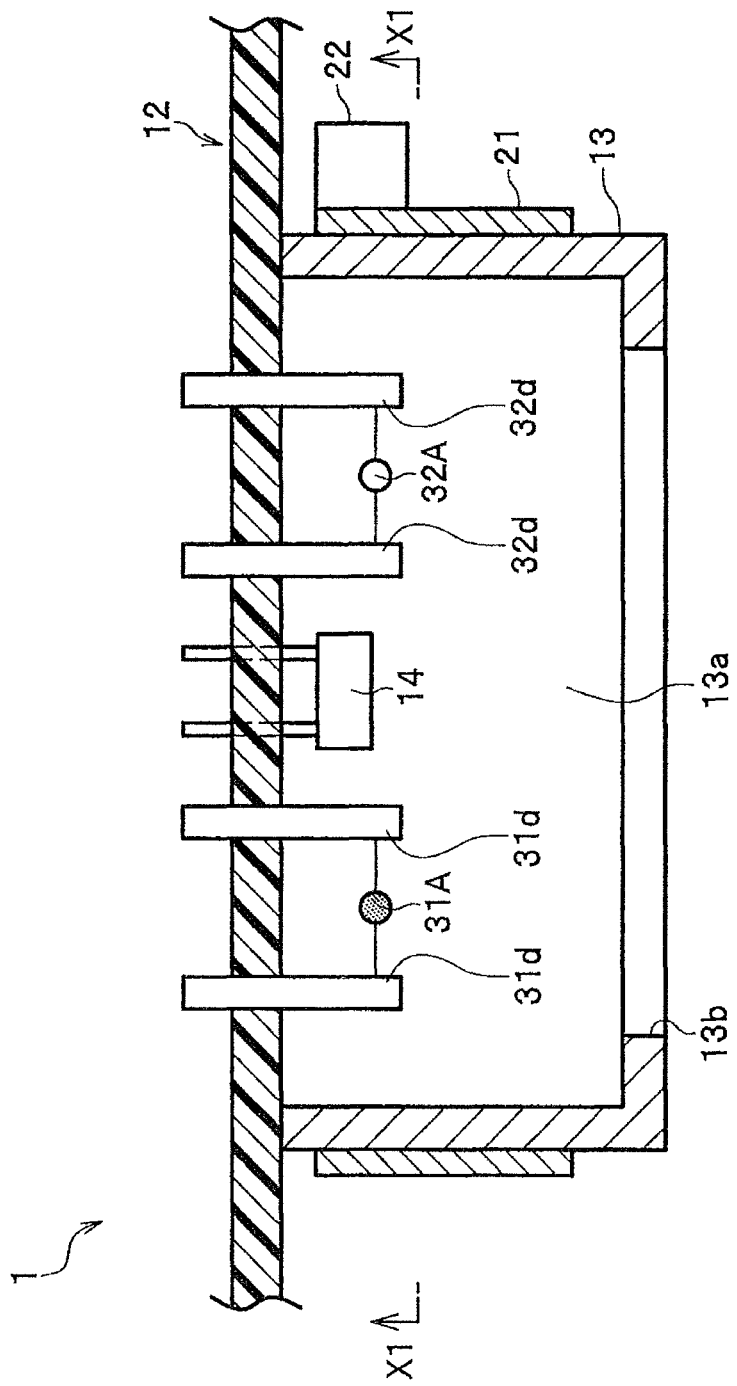
FIG. 3 is an enlarged vertical sectional view of the hydrogen sensor according to the first embodiment taken along the line X2-X2 of FIG. 4.

The first detection element 31A extends vertically downward from the substrate 11, and is fixed to lower ends of metallic stays 31d of the first serial side in the detection chamber 13a (see FIGS. 2-4). On the other hand, like the first detection element 31A, the first compensation element 32A extends vertically downward from the substrate 11, and is fixed to lower ends of metallic stays 32d of the first serial side 30 in the detection chamber 13a.

The first detection element 31A is a well known element which is active to hydrogen, is referred to as a catalytic resistor, and is provided with a coil 31a, a spherical carrier 31b for coating the coil 31a, and a catalyst oxide 31c supported by the carrier 31b.

Like the heater 21, the coil 31a is made of a material whose temperature resistance coefficient is large such as platinum (Pt), etc. The carrier 31b is a porous body made of alumina, etc. The catalyst oxide 31c is made of a noble metal (platinum, etc.) which is active to hydrogen and oxidizes (burns) hydrogen.

However, the shape of the first detection element 31A is not limited the coil-shape, a thin-film type may be used.

Accordingly, the temperature and the resistor value $R_{31}$ of the first detection element 31A are changed based on (1) the temperature (the atmospheric temperature, an ambient temperature) of the detection chamber 13a, and (2) a heat of combustion generated by combustion (oxidation) contact between the hydrogen and the catalyst oxide 31c.

The first compensation element 32A is a well known element which is inactive to hydrogen, and is provided with a coil 32a, a spherical carrier 32b for coating the coil 32a, and an inactive layer (not shown) for coating the carrier 32b so as to be inactive to the hydrogen.

The inactive layer is made of a non-metal such as alumina ($Al_2O_3$) or silica ($SiO_2$), etc. or a metal such as gold (Au), etc. which does not react to the hydrogen. Also, if the first compensation element 32A contacts the hydrogen, the hydrogen does not show a catalytic combustion reaction and does not generate the heat of combustion.

Accordingly, the temperature and the resistor value $R_{32}$ of the first compensation element 32A are changed based on only the temperature (the atmospheric temperature, the ambient temperature) of the detection chamber 13a.

First Bridge Circuit—Second Serial Side

The second serial side 40 is provided with a first resistor 41 (resistor value $R_{41}$) and a second resistor 42 (resistor value $R_{42}$), and the first resistor 41 is connected to the second resistor 42 in series. The first resistor 41 and the second resistor 42 are mounted on the substrate 11 (see FIG. 2). The resistor value $R_{41}$ of the first resistor 41 and the resistor value $R_{42}$ of the second resistor 42 are fixed values.

Connection State of First Serial Side and Second Serial Side

Both ends of the first serial side 30 and both ends of the second serial side 40 are connected to an input terminal T1 and an input terminal T2 respectively. The input terminal T1 and the input terminal T2 are connected to the voltage generation circuit 53, and a voltage VIN generated by the voltage generation circuit 53 is applied to the input terminals T1 and T2 so as to energize the first bridge circuit B1.

In the first serial side 30, a middle point between the first detection element 31A and the first compensation element 32A serves as an output terminal T3. In the second serial side 40, a middle point between the first resistor 41 and the second resistor 42 serves as an output terminal T4. Also, the output terminal T3 and the output terminal T4 are connected to the microcomputer 51, and a potential difference $V1_{OUT}$ (a first signal) of the first bridge circuit B1 is output to the microcomputer 51.

That is, although the resistor value $R_{41}$ of the first resistor 41 and the resistor value $R_{42}$ of the second resistor 42 are fixed value, the resistor value $R_{31}$ of the first detection element 31A is changed based on (1) the temperature of the detection chamber 13a, and (2) the heat of combustion of the hydrogen, the resistor value $R_{32}$ of the first compensation element 32A is changed based on (1) the temperature of the detection chamber 13a, and the potential difference $V1_{OUT}$ between the output terminals T3 and T4 based on a difference the resistor value $R_{31}$ and the resistor value $R_{32}$ is output to the microcomputer 51 as the first signal of the first bridge circuit B1.

Here, when the temperature in the detection chamber 13a is as a room temperature (25 degrees, etc.) and the hydrogen concentration is zero, the resistor value $R_{31}$ of the first detection element 31A, the resistor value $R_{32}$ of the first compensation element 32A, the resistor value $R_{41}$ of the first resistor 41, and the resistor value $R_{42}$ of the second resistor 42 are set so that the potential difference $V1_{OUT}$ of the first bridge circuit B1 becomes 0.

Also, since the resistor value $R_{31}$ of the first detection element 31A and the resistor value $R_{32}$ of the first compensation element 32A are changed in response to the temperature of the detection chamber 13a in the same way, the potential difference $V1_{OUT}$ of the first bridge circuit B1 is changed in response to the hydrogen concentration.

<Second Bridge Circuit>

The second bridge circuit B2 has the same structure as that of the first bridge circuit B1, is energized at the time when deterioration of the normal detection element pair P1 (the first detection element 31A, and the first compensation element 32A) of the first bridge circuit B1 is determined, and outputs a potential difference $V2_{OUT}$ (a second signal) to the microcomputer 51 as a deterioration standard.

That is, compared to the first bridge circuit B1, the second bridge circuit B2 is provided with the second detection element 31B instead of the first detection element 31A, and the second compensation element 32B instead of the first compensation element 32A. The second detection element 31B and the second compensation element 32B are placed in the detection chamber 13a (see FIGS. 2-4). Also, the reference detection element pair P2 is composed of a pair of the second detection element 31B and the second compensation element 32B.

The second detection element 31B has the same structure as that of the first detection element 31A, and the resistor value $R_{31}$ is changed based on (1) the temperature of the detection chamber 13a, and (2) the heat of combustion of the hydrogen. The second compensation element 32B has the same structure as that of the first compensation element 32A, and the resistor value $R_{32}$ is changed based on (1) the temperature of the detection chamber 13a.

Also, a potential difference $V2_{OUT}$ between the output terminals T3 and T4 of the second bridge circuit B2 is output to the microcomputer 51 as the second signal of the second bridge circuit B2.

<Arrangement State of First Detection Element, etc.>

Here, with reference to FIG. 4, an arrangement state of the first detection element 31A, the first compensation element 32A, the second detection element 31B, and the second compensation element 32B will be explained. In addition, the first detection element 31A and the second detection element 31B generate the heat of combustion when they contact the hydrogen.

A first arrangement direction D1 of the first detection element 31A and the first compensation element 32A is parallel to a second arrangement direction D2 of the second detection element 31B and the second compensation element 32B. Here, the first arrangement direction D1 and second arrangement direction D2 are parallel to a direction of an off gas flowing through the pipe 120a (i.e., a right-to-left direction in FIG. 2). However, the first arrangement direction D1 and the second arrangement direction D2 are not limited to the above. For example, the first arrangement direction D1 and the second arrangement direction D2 may be perpendicular to the direction of the off gas flowing through the pipe 120a (i.e., a front-to-back direction in FIG. 2).

Also, the normal detection element pair P1 and the reference detection element pair P2 are placed at a predetermined space in a fifth arrangement direction D5 which perpendicular to the first arrangement direction D1 and the second arrangement direction D2 (i.e., an up-to-down direction in FIG. 4).

Also, in the horizontal plane, the first sequential order of the first detection element 31A and the first compensation element 32A of the normal detection element pair P1 is reverse to the second sequential order of the second detection element 31B and the second compensation element 32B of the reference detection element pair (see FIG. 4).

For this reason, the first detection element 31A, the first compensation element 32A, the second detection element 31B, and the second compensation element 32B are placed at apexes of the virtual rectangle (preferably, square), and the first detection element 31A and the second detection element 31B are placed counter-cornered in the virtual rectangle. In this way, the first detection element 31A and the second detection element 31B, which generate heat by combustion of the hydrogen, are placed separately from each other. Therefore, the thermal interference can hardly occur between the first detection element 31A and the second detection element 31B compared to the structure in which the first detection element 31A and the second detection element 31B are placed in the fifth arrangement direction D5.

That is, it becomes difficult to change the temperature and the resistor value $R_{31}$ of the first detection element 31A by the heat from the second detection element 31B, and it becomes difficult to change the temperature and the resistor value $R_{31}$ of the second detection element 31B by the heat from the first detection element 31A. Accordingly, the potential difference $V1_{OUT}$ (the first signal) of the first bridge circuit B1 (the normal detection element pair P1) and the potential difference $V2_{OUT}$ (the second signal) of the second bridge circuit B2 (the reference detection element pair P2) can be changed easily in response to only the hydrogen concentration. Therefore, the hydrogen concentration can be detected with high accuracy. Also, the microcomputer 51 preferably determines the deterioration of the normal detection element pair P1.

<Microcomputer>

The hydrogen sensor 1 is provided with a microcomputer 51 (a control unit, a correction unit). The microcomputer 51 is provided with a CPU, a ROM, a RAM, a variety of interfaces, and an electronic circuit, etc., and shows a variety of functions in accordance with a stored program.

<Microcomputer—Heater Control Function>

In particular, the microcomputer 51 performs control (PWM control, ON/OFF control, etc.) of the heater driving circuit 52 based on the temperature of the heater 21 input from the temperature sensor 22 (and/or the temperature of the detection chamber 13a input from the temperature sensor 14) so that the temperature of the detection chamber 13a becomes equal to or greater than a target temperature. For example, the target temperature is set at equal to or greater than the temperature which prevents the off gas from condensing in the detection chamber 13a.

<Microcomputer—Voltage Control Function>

Also, the microcomputer 51 controls the voltage generation circuit 53 (1) to apply a predetermined voltage to the first bridge circuit B1 at the time of normal operation, and (2) to apply a predetermined voltage to the first bridge circuit B1 and the second bridge circuit B2 (the reference detection element pair P2) at the time when deterioration of the first bridge circuit B1 (the normal detection element pair P1). In addition, for example, the deterioration of the first bridge circuit B1 is determined (1) when an integrated hours-of-operation of the hydrogen sensor 1 achieves a predetermined hours, and (2) when an integrated hydrogen concentration achieves a predetermined concentration, etc.

<Microcomputer—Correction Function>

Also, the microcomputer 51 (the correction unit) multiplies the potential difference $V1_{OUT}$ (the first signal) of the first bridge circuit B1 (the normal detection element pair P1) by a correction coefficient α so as to correct the potential difference $V1_{OUT}$. For this reason, the potential difference $V1_{OUT}$ is corrected based on an individual difference between the first detection element 31A and the first compensation element 32A (i.e., the difference between the resistor value $R_{31}$ and the resistor $R_{32}$ caused by change in the temperature when the atmospheric temperatures are the same). That is, the potential difference $V1_{OUT}$ is corrected in response to only the hydrogen concentration.

Figure 6:
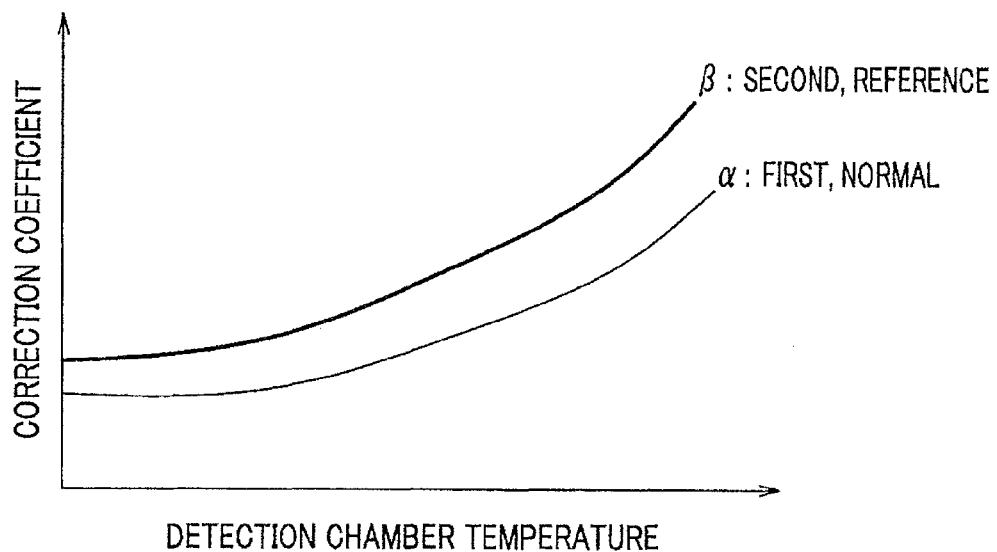
FIG. 6 is a map showing a relationship between a temperature of a detection chamber and correction coefficients α and β.

Here, the correction coefficient α is calculated based on the temperature in the detection chamber 13a and a map shown in FIG. 6. As shown in FIG. 6, the higher the temperature in the detection chamber 13a, the larger the correction coefficient α. The reason is that it is difficult to harmonize the coil 31a and the carrier 31b of the first detection element 31A with the coil 32a and the carrier 32b of the first compensation element 32A in specification (length and thickness of the coils, and size of the carrier, etc.), and that a difference between the resistor value $R_{31}$ of the first detection element 31A and the resistor value $R_{32}$ of the first compensation element 32A occurs when the hydrogen concentration is zero as shown in FIG. 7, and that the difference between the resistor values is changed in response to change in the temperature of the detection chamber 13a.

Figure 7:
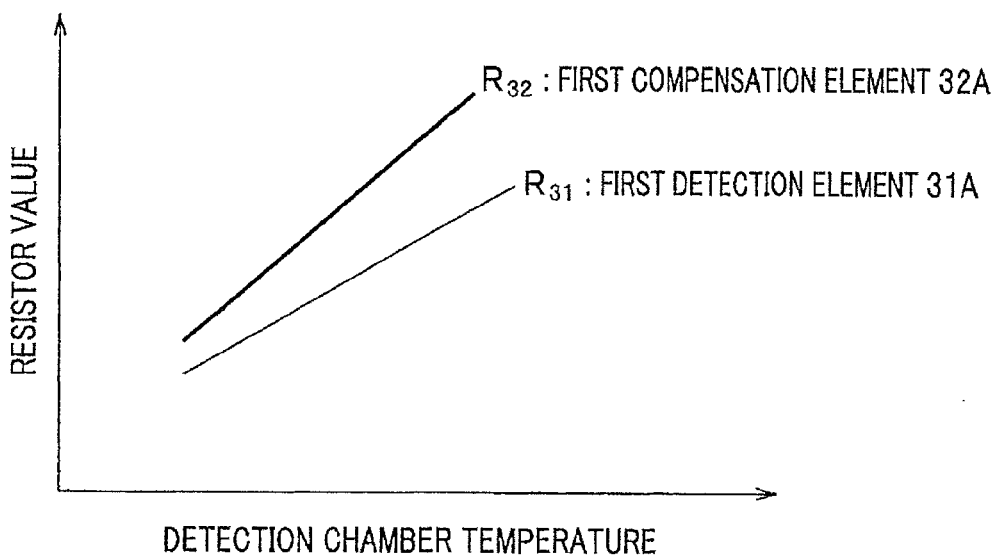
FIG. 7 is a graph showing a relationship between the temperature of the detection chamber and a resistor value.

In addition, as shown in FIG. 7, the resistor value $R_{32}$ of the first compensation element 32A is greater than the resistor value $R_{31}$ of the first detection element 31A, and the higher the temperature in the detection chamber 13a, the larger the difference between the resistor value $R_{32}$ and the resistor value $R_{31}$. Also, as shown in FIG. 6, the higher the temperature in the detection chamber 13a, the larger the correction coefficient α. However, the present invention is not limited to the above. The above relationships may be reversed depending on the specifications of the first detection element 31A and the first compensation element 32A, and the direction in which the voltage is applied to first bridge circuit B1, etc. Also, the map shown in FIG. 6 is calculated by an experiment in advance, and is stored in the microcomputer 51.

Likewise, the microcomputer 51 multiplies the potential difference $V2_{OUT}$ (the second signal) of the second bridge circuit B2 (the reference detection element pair P2) by a correction coefficient β so as to correct the potential difference. For this reason, potential difference $V2_{OUT}$ is corrected based on an individual difference between the second detection element 31B and the second compensation element 32B. That is, the potential difference $V2_{OUT}$ is corrected in response to only the hydrogen concentration.

Also, the microcomputer 51 outputs a corrected potential difference $V1_{OUT}$ (or a converted signal thereof) to the ECU 130 in response to the hydrogen concentration at the time of normal operation.

<Microcomputer—Deterioration Determination Function>

Also, the microcomputer 51 (a deterioration determination unit) determines whether the normal detection element pair P1 (especially, the first detection element 31A) of the first bridge circuit B1 deteriorates or not.

In particular, the microcomputer 51 determines that the normal detection element pair P1 deteriorates when the difference between the corrected potential difference $V1_{OUT}$ (the first signal) and the corrected potential difference $V2_{OUT}$ (the second signal) is equal to or greater than a predetermined value. The predetermined value is a value at which it is determined that the normal detection element pair P1 deteriorates, is determined by an experiment in advance, and is stored in the microcomputer 51. In addition, when the deterioration of the first detection element 31A of the normal detection element pair P1 proceeds, a catalytic function of the catalyst oxide 31c is lowered and the resistor value $R_{31}$ is decreased.

Also, when the microcomputer 51 determines that the normal detection element pair P1 deteriorates, the microcomputer 51 outputs a signal (a deterioration signal) to the ECU 130.

<Heater Driving Circuit, Voltage Generation Circuit>

The hydrogen sensor 1 is provided with a heater driving circuit 52 and a voltage generation circuit 53.

The heater driving circuit 52 is provided with a DC-DC converter, etc., and is connected to an outer power source 61 (12V battery, etc.). Also, the heater driving circuit 52 supplies an electric power from an outer power source 61 to the heater 21 in accordance with an instruction from the microcomputer 51 while changing a current value of the electric power.

The voltage generation circuit 53 is provided with a DC-DC converter, etc., and is connected to an outer power source 62 (e.g., 12V battery). Also, in accordance an instruction from the microcomputer 51, the voltage generation circuit 53 applies a predetermined voltage (1) to the first bridge circuit B1 at the time of normal operation, and (2) to the first bridge circuit B1 and the second bridge circuit B2 at the time when deterioration of the normal detection element pair P1 is determined.

<<Operation of Hydrogen Sensor>>

Figure 8:
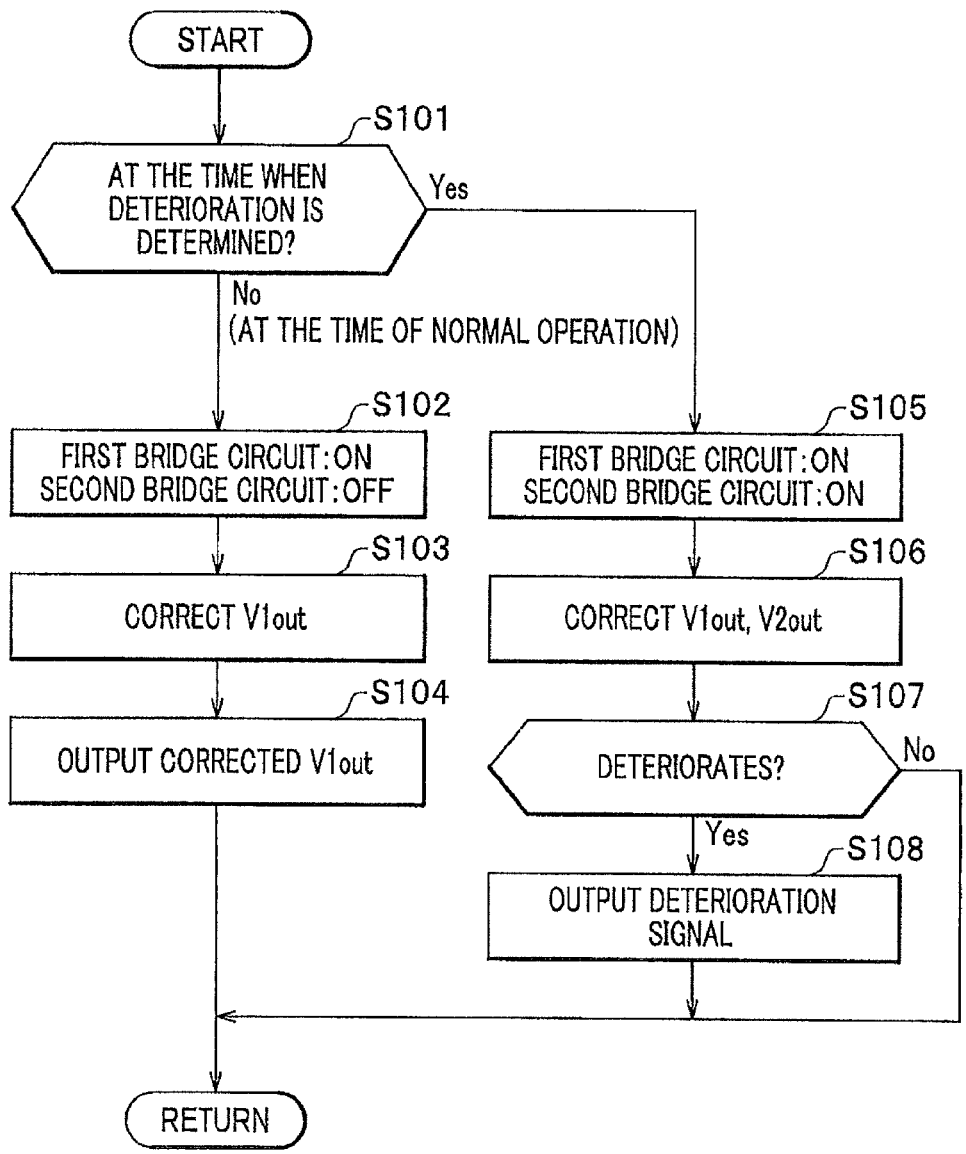
FIG. 8 is a flowchart showing an operation of the hydrogen sensor according to the first embodiment.

Next, with reference to FIG. 8, operation of the hydrogen sensor 1 will be explained. In addition, the microcomputer 51 repeats a series of process steps of FIG. 8 in accordance with an instruction from the ECU 130 which detects an ON signal of the IG 131.

In step S101, the microcomputer 51 determines whether the present time is the time when deterioration of the normal detection element pair P1 is determined or not.

If the microcomputer 51 determines that the present time is the time when deterioration is determined (S101: Yes), the process of the microcomputer 51 proceeds to step S105. On the other hand, If the microcomputer 51 determines that the present time is not the time when deterioration is determined (S101: No), the process of the microcomputer 51 proceeds to step S102. In addition, if the process of the microcomputer 51 proceeds to step S102, the present time is the time of normal operation.

In step S102, the microcomputer 51 controls the voltage generation circuit 53 so as to apply the predetermined voltage to the first bridge circuit B1. In addition, the second bridge circuit B2 is turned OFF.

In step S103, the microcomputer 51 corrects the potential difference $V1_{OUT}$ of the first bridge circuit B1.

In particular, the microcomputer 51 calculates the correction coefficient α based on the temperature of the detection chamber 13a and the map shown in FIG. 6, and multiplies the potential difference $V1_{OUT}$ by the correction coefficient α so as to obtain the corrected potential difference $V1_{OUT}$.

In step S104, the microcomputer 51 outputs the corrected potential difference $V1_{OUT}$ (or a signal corresponding to the corrected potential difference $V1_{OUT}$) to the ECU 130.

After that, the process of the microcomputer 51 returns to "START" via "RETURN".

In step S105, the microcomputer 51 controls the voltage generation circuit 53 so as to apply predetermined voltages to the first bridge circuit B1 and the second bridge circuit B2 respectively.

In step S106, the microcomputer 51 corrects the potential difference $V1_{OUT}$ of the first bridge circuit B1 and the potential difference $V2_{OUT}$ of the second bridge circuit B2 respectively.

In step S107, the microcomputer 51 determines whether the normal detection element pair P1 deteriorates or not. For example, if an absolute value of the difference between the corrected potential difference $V1_{OUT}$ and the corrected potential difference $V2_{OUT}$ is equal to or greater than a predetermined value, the microcomputer 51 determines that the normal detection element pair P1 deteriorates.

If the microcomputer 51 determines that the normal detection element pair P1 deteriorates (S107: Yes), the process of the microcomputer 51 proceeds to step S108. On the other hand, If the microcomputer 51 determines that the normal detection element pair P1 does not deteriorate (S107: No), the process of the microcomputer 51 returns to "START" via "RETURN".

In step S108, the microcomputer 51 outputs a deterioration signal corresponding that the normal detection element pair P1 deteriorates to the ECU 130.

In this case, the ECU 130 preferably activates an alarm unit such as a warning lamp (not shown) so as to inform an operator that the normal detection element pair P1 deteriorates.

After that, the process of the microcomputer 51 returns to "START" via "RETURN".

<<Effect of Hydrogen Sensor>>

According to the above hydrogen sensor 1, following effects can be obtained.

Since the hydrogen sensor 1 is provided with one element housing 13, the hydrogen sensor 1 can be minimized easily and can be manufactured at low cost.

Since the first detection element 31A and the second detection element 31B are placed separated from each other, the thermal interference can hardly occur between the first detection element 31A and the second detection element 31B, the hydrogen concentration can be detected with high accuracy, and the deterioration of the normal detection element pair P1 can be determined accurately.

Since only one element housing 13 and only one detection chamber 13a are provided, they can be heated by only one heater 21. For this reason, the number of parts of the heater 21 is minimized, and the hydrogen sensor 1 can be manufactured at low cost.

Since the first detection element 31A, the first compensation element 32A, the second detection element 31B, and the second compensation element 32B are placed around the temperature sensor 14, the temperature detected by the temperature sensor 14 becomes to the atmospheric temperature of the first detection element 31A, etc. easily.

Also, since the microcomputer 51 corrects the potential differences $V1_{OUT}$ and $V2_{OUT}$ based on the temperature detected by the temperature sensor 14, the hydrogen concentration can be detected with high accuracy, and the deterioration of the normal detection element pair P1 can be determined accurately.

<<Modifications>>

Although one embodiment of the present invention has been described, the present invention is not limited to thereto. The embodiment may be combined with structures descried later, or may be modified as follows.

Although the detected gas is hydrogen in the above described embodiment, the detected gas may be other gas.

Although the hydrogen sensor 1 is the catalytic combustion type hydrogen sensor in the above described embodiment, other type (e.g., a thermal conductive type, a proton type, or a semiconductor type, etc.) hydrogen sensor may be used.

Although the fuel cell system 100 is mounted on the fuel cell vehicle in the above described embodiment, the fuel cell system 100 may be mounted on other mobile units such as a two-wheeled vehicle, a train, or a ship, etc. Also, the present invention may be applied to a domestic fuel cell system, or a fuel cell system for a hot-water supply system.

<<Second Embodiment>>

Figure 9:
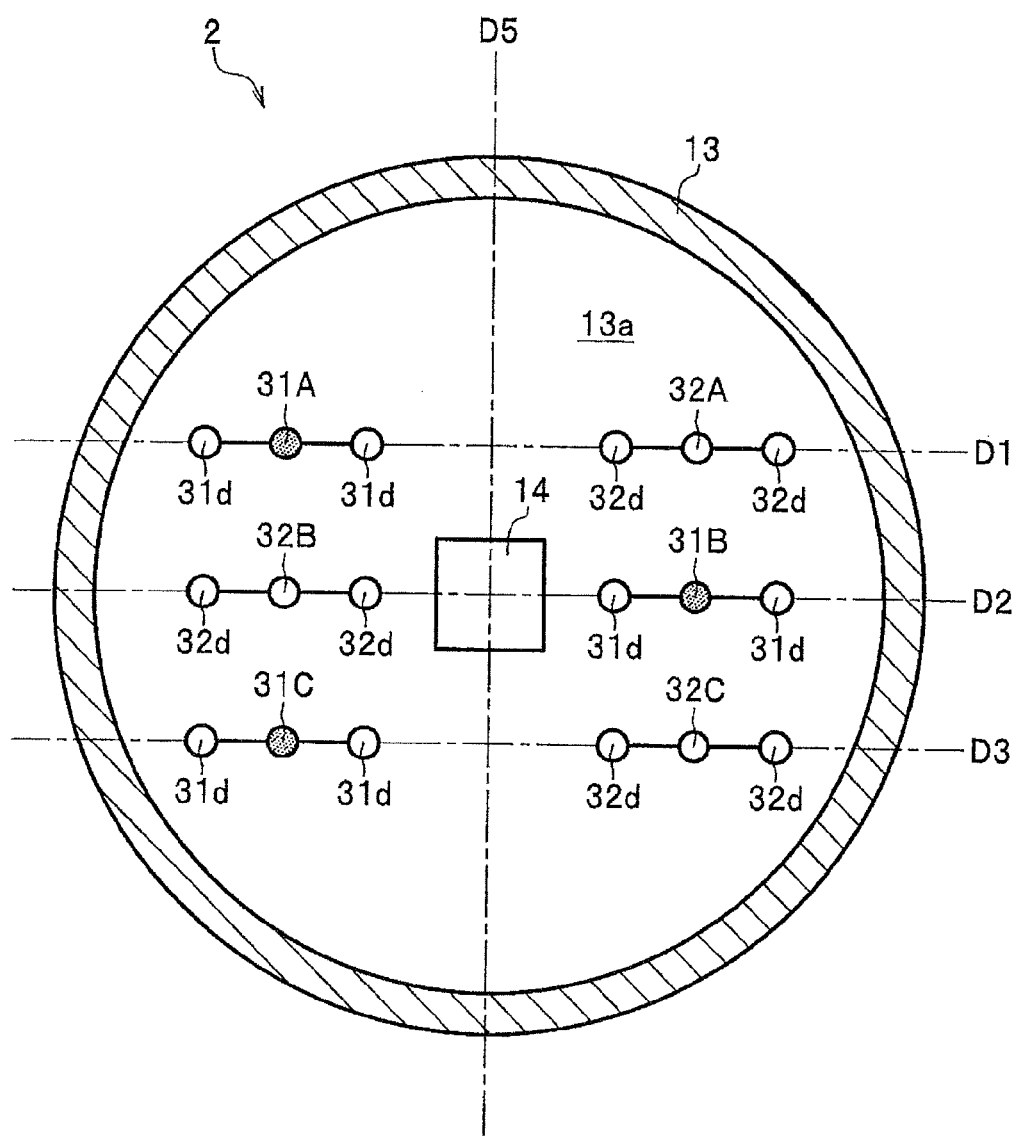
FIG. 9 is a horizontal sectional view of a hydrogen sensor according to a second embodiment taken along the line X1-X1 of FIG. 3.

Next, with reference to FIG. 9, a second embodiment of the present invention will be explained. In addition, only different points from the first embodiment will be explained.

A hydrogen sensor 2 according to a second embodiment is provided with a normal detection element pair P3 which differs from the normal detection element pair P1. Also, for example, at the time of normal operation, the normal detection element pair P1 and the normal detection element pair P3 are alternately activated every predetermined time so as to increase lives of the normal detection element pair P1 and the normal detection element pair P3.

The normal detection element pair P3 is composed of a pair of a third detection element 31C and a third compensation element 32C. In addition, the hydrogen sensor 1 is provided with a third bridge circuit (not shown) like the first bridge circuit B1, and the third bridge circuit (not shown) is composed of the normal detection element pair P3.

A third arrangement direction D3 of the third detection element 31C and the third compensation element 32C is parallel to the first arrangement direction D1 and the second arrangement direction D2.

Also, the normal detection element pair P3 is placed symmetrical with respect to the reference detection element pair P2 at a side opposite to the normal detection element pair P1, and is placed in the fifth arrangement direction D5 at a predetermined space from the reference detection element pair P2.

Further, a third sequential order of the third detection element 31C and the third compensation element 32C of the normal detection element pair P3 is reverse to the second sequential order of the second detection element 31B and the second compensation element 32B of the reference detection element pair P2.

For this reason, since the third detection element 31C of the normal detection element pair P3 and the second detection element 31B of the reference detection element pair P2 are placed separated from each other, the thermal interference can be reduced between the third detection element 31C and the second detection element 31B.

Although two normal detection element pairs P1 and P3, and one reference detection element pair P2 are provided in the above described embodiment, for example, one normal detection element pair and two reference detection element pairs may be provided. In this case, one normal detection element pair is placed between two reference detection element pairs in the fifth arrangement direction D5.

Also, two normal detection element pairs and two reference detection element pairs may be provided. In this case, the reference detection element pairs and the normal detection element pair are alternately placed in the fifth arrangement direction D5.

<<Third Embodiment>>

Figure 10:
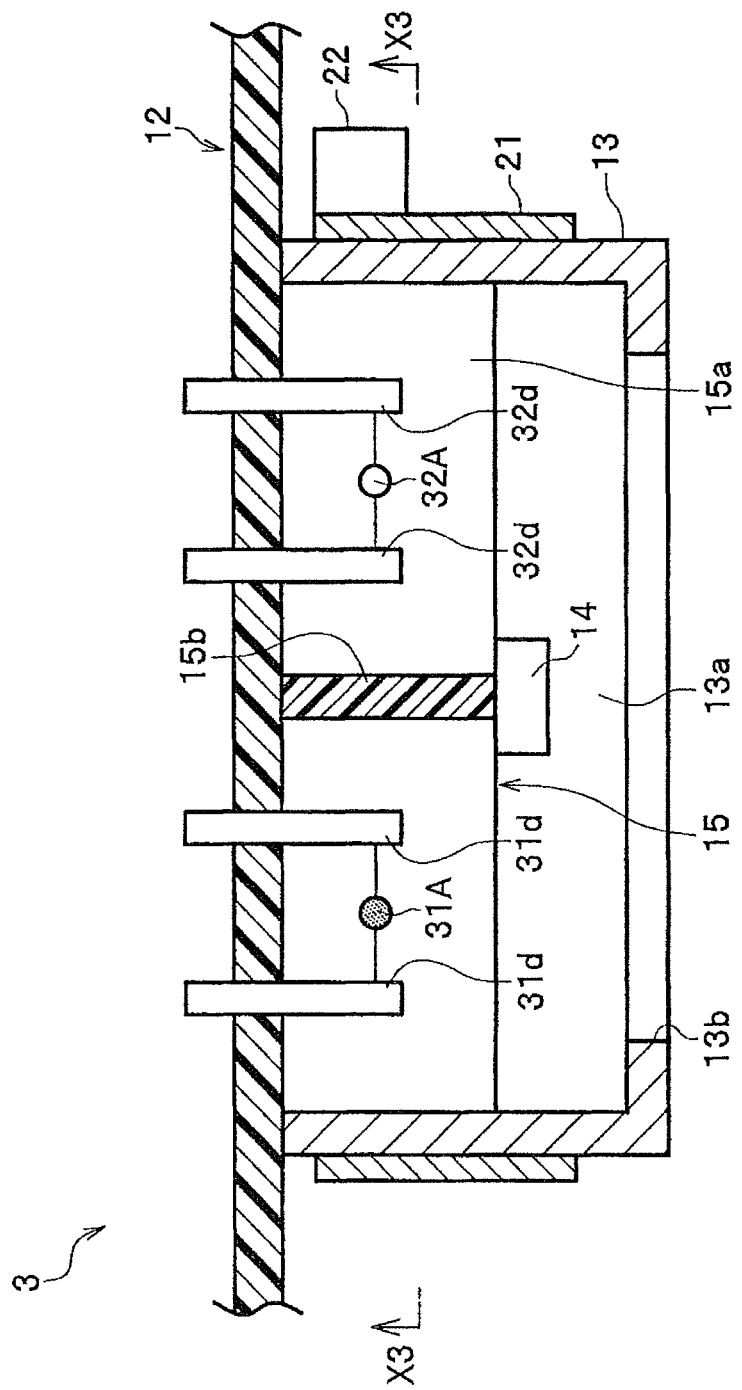
FIG. 10 is an enlarged vertical sectional view of a hydrogen sensor according to a third embodiment taken along the line X4-X4 of FIG. 11.
Figure 11:
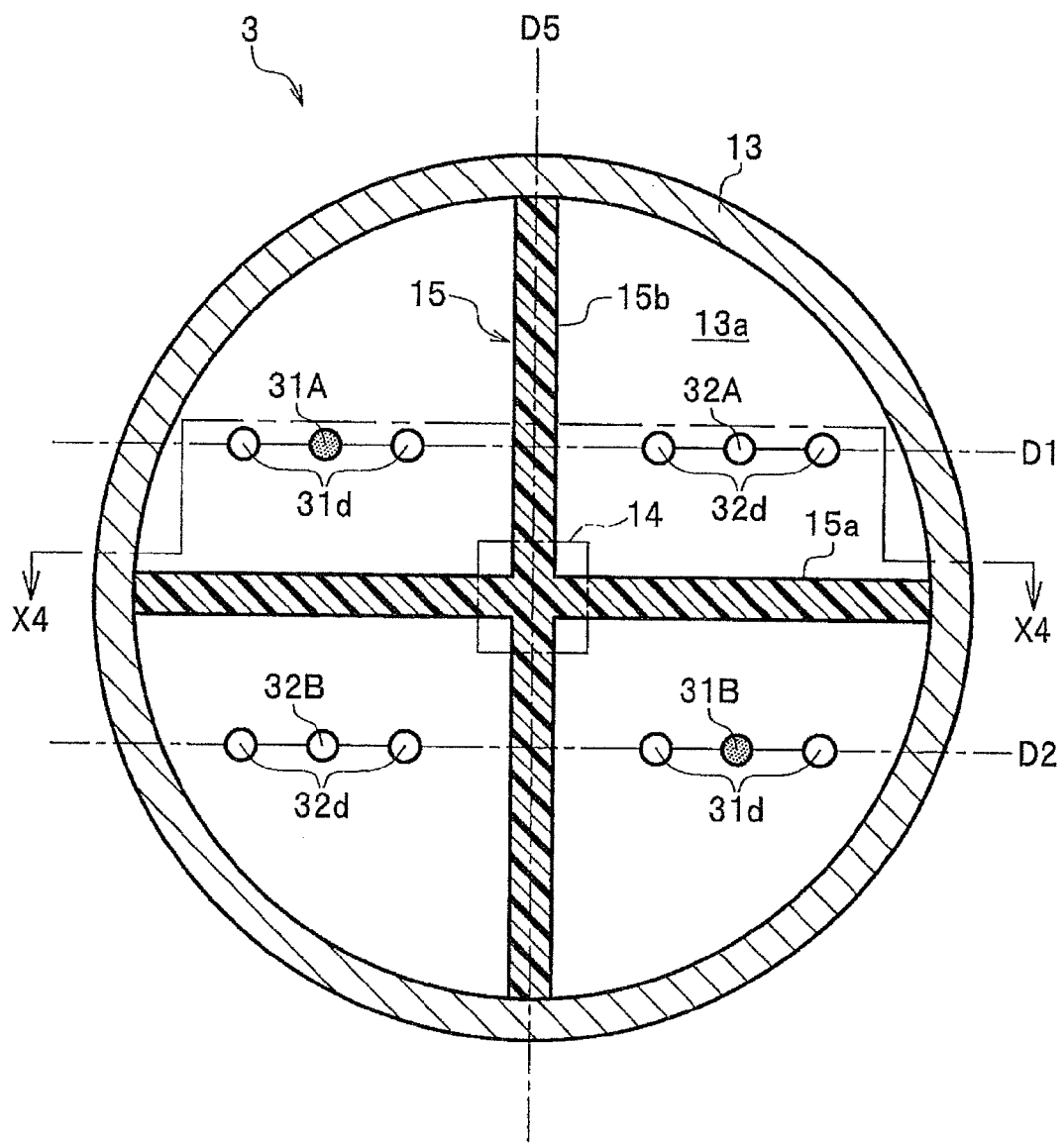
FIG. 11 is a horizontal sectional view of the hydrogen sensor according to the third embodiment taken along the line X3-X3 of FIG. 10.

Next, with reference to FIGS. 10-11, a third embodiment of the present invention will be explained. In addition, only different points from the first embodiment will be explained.

A hydrogen sensor 3 according to the third embodiment is provided with a cross-shaped insulating member 15 which is made of a resin (e.g., polyphenylene sulfide. etc.). However, the insulating member 15 may be a corrosion-resistant metal (e.g., SUS, etc.).

The insulating member 15 is provided with a first wall 15a and a second wall 15b crossing at a mid points thereof in the horizontal plane. The first wall 15a extends between the normal detection element pair P1 and the reference detection element pair P2 in a direction parallel to the first arrangement direction D1 and the second arrangement direction D2. The second wall 15b extends between the first detection element 31A and the first compensation element 32A of the normal detection element pair P1, and between the second detection element 31B and the second compensation element 32B of the reference detection element pair P2, in a direction parallel to the fifth arrangement direction.

In addition, the insulating member 15 extends vertically downward from a bottom of the casing 12 to a position which is lower than the first detection element 31A, etc. Also, the temperature sensor 14 is provided at a cross point of the first wall 15a and the second wall 15b.

According to the hydrogen sensor 3, the first wall 15a extends between the normal detection element pair P1 and the reference detection element pair P2, and the second wall 15b extends between the first detection element 31A and the first compensation element 32A, and between the second detection element 31B and the second compensation element 32B. As a result, the thermal interference among the first detection element 31A, the first compensation element 32A, the second detection element 31B, and the second compensation element 32B can be reduced.

Although the insulating member 15 is cross-shaped in third embodiment, for example, the second wall 15b extending in the fifth arrangement direction D5 may be omitted. According to the above structure, the atmospheric temperature of the first detection element 31A becomes equal to the atmospheric temperature of the first compensation element 32A easily. Likewise, the atmospheric temperature of the second detection element 31B becomes equal to the atmospheric temperature of the second compensation element 32B easily.

<<Fourth Embodiment>>

Figure 12:
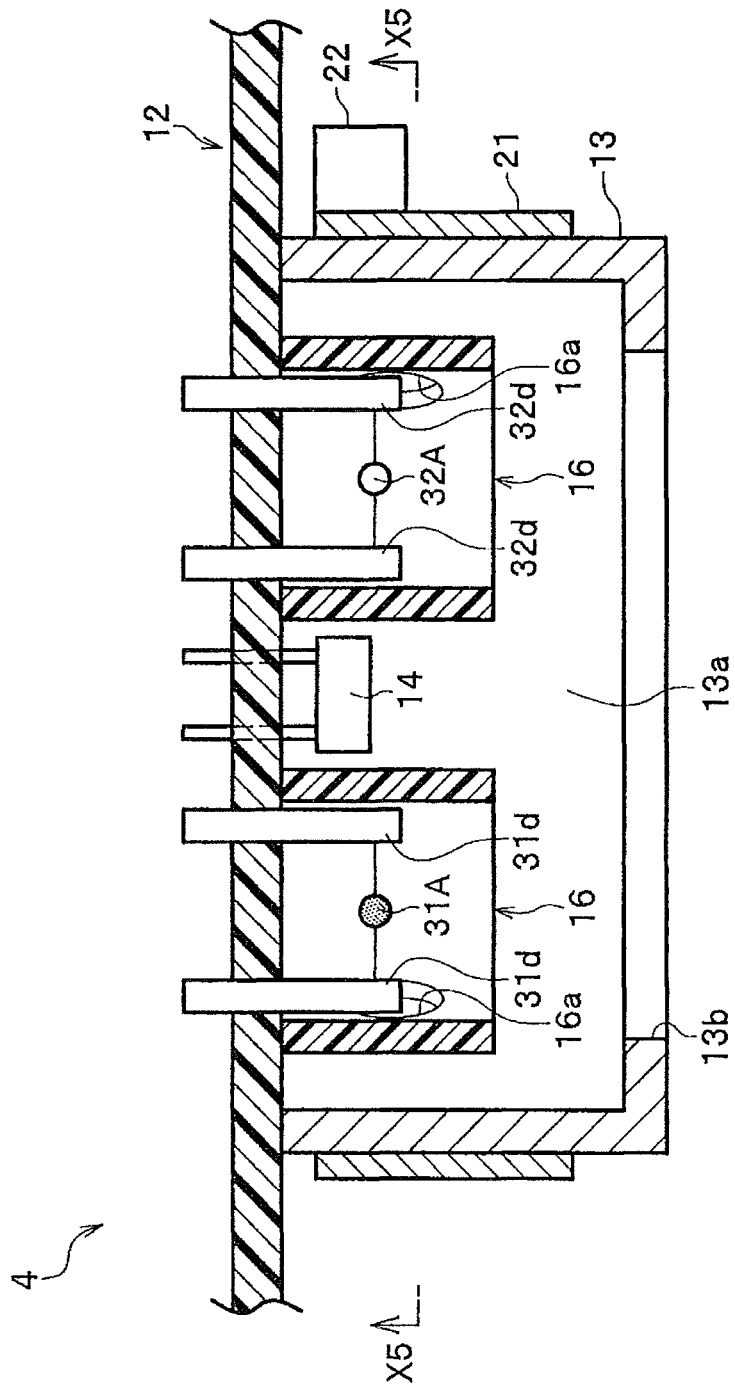
FIG. 12 is an enlarged vertical sectional view of a hydrogen sensor according to a fourth embodiment taken along the line X6-X6 of FIG. 13.
Figure 13:
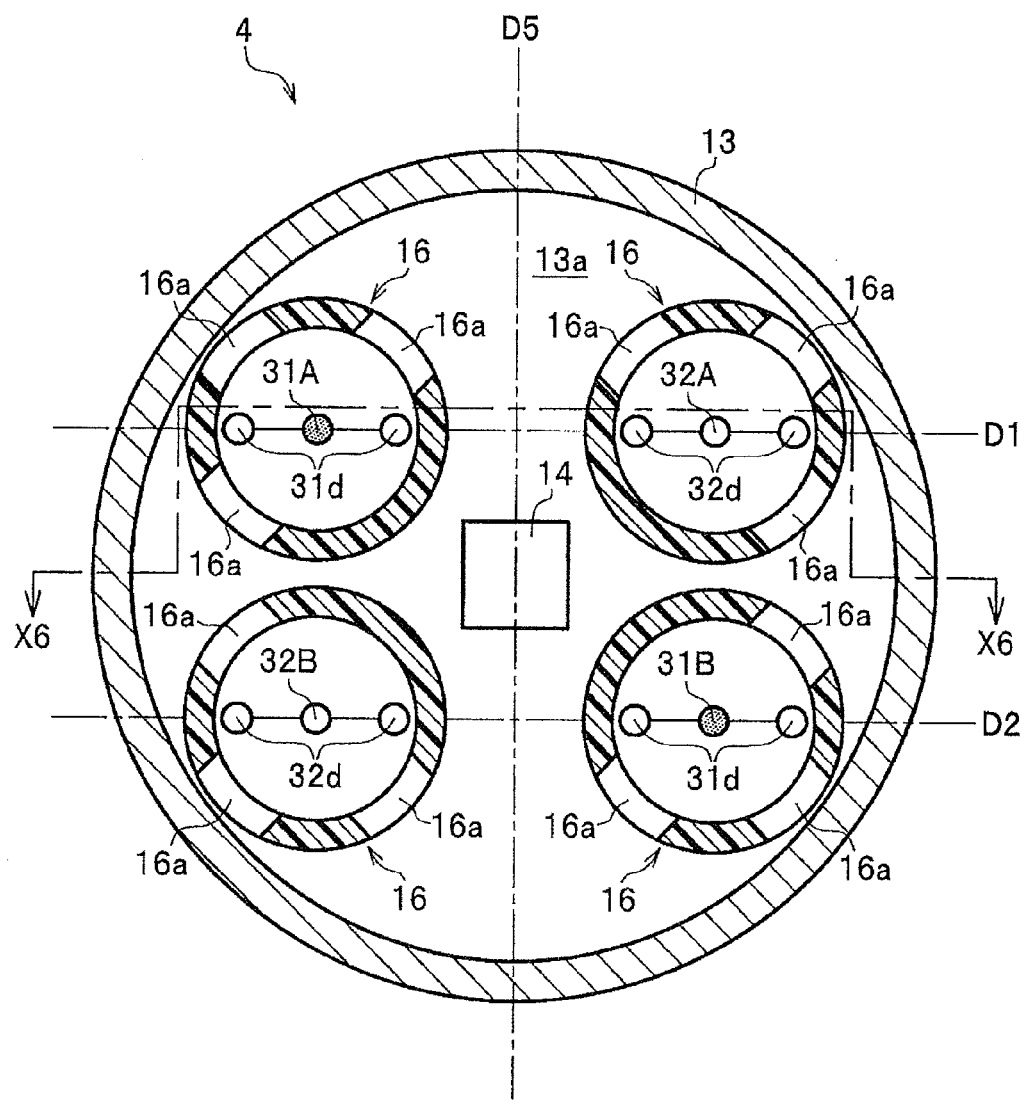
FIG. 13 is a horizontal sectional view of the hydrogen sensor according to the fourth embodiment taken along the line X5-X5 of FIG. 12.

Next. with reference to FIGS. 12-13, a fourth embodiment of the present invention will be explained. In addition, only different points from the first embodiment will be explained.

A hydrogen sensor 4 according to the fourth embodiment is provided with four cylindrical insulating members 16. However, the shape of the insulating member 16 is not limited to the cylindrical-shape, a polygonal-tube shape (e.g., a hexagonal-tube shape) may be used.

The four insulating members 16 extend vertically downward from the bottom of the casing 12, and surround the first detection element 31A, the first compensation element 32A, the second detection element 31B, and the second compensation element 32B respectively. For this reason, the thermal interference among the first detection element 31A, the first compensation element 32A, the second detection element 31B, and the second compensation element 32B can be reduced.

Also, the insulating members 16 may surround only the first detection element 31A and the second detection element 31B.

Three through holes 16a are formed on the side wall of the cylindrical insulating member 16. The off gas containing hydrogen passes through the through hole 16a. Also, the through hole 16a may be omitted.

The three through holes 16a are formed at an angle of 45 degrees to the first arrangement direction D1 or the second arrangement direction D2. That is, the through hole 16a is not formed in a direction from one element (e.g., the first detection element 31A) to the nearest element (e.g., the first compensation element 32A or the second compensation element 32B).

For this reason, the thermal interference between adjacent elements (e.g., between the first detection element 31A and the first compensation element 32A) in the first arrangement direction D1 (the second arrangement direction D2) or the fifth arrangement direction D5 can be reduced.

However, the through hole 16a is not formed counter-cornered in the virtual rectangle whose apexes are the first detection element 31A, etc. For this reason, the thermal interference between the first detection element 31A and the second detection element 31B, and the first compensation element 32A and the second compensation element 32B can be reduced.

What is claimed is:

1. A gas sensor, comprising:
a normal detection element pair which has a first detection element whose temperature is raised and whose resistor value is changed by contact with a detected gas and a first compensation element which is inactive to the detected gas, and outputs a first signal corresponding to a concentration of the detected gas based on a difference between the resistor value of the first detection element and a resistor value of the first compensation element;
a reference detection element pair which has a second detection element whose temperature is raised and whose resistor value is changed by contact with the detected gas and a second compensation element which is inactive to the detected gas, and outputs a second signal which is used as a deterioration standard corresponding to the concentration of the detected gas based on a difference between a resistor value of the second detection element and a resistor value of the second compensation element at the time when deterioration of the normal detection element pair is determined;
an element housing which has a detection chamber which houses both of the normal detection element pair and the reference detection element pair;
a temperature sensor which is placed in the detection chamber and is used for detecting a temperature in the detection chamber; and
a correction unit for correcting the first signal of the normal detection element pair and the second signal of the reference detection element pair based on the temperature in the detection chamber detected by the temperature sensor respectively,
wherein
a first arrangement direction of the first detection element and the first compensation element is parallel to a second arrangement direction of the second detection element and the second compensation element,
the normal detection element pair and the reference detection element pair are placed in a direction which is perpendicular to the first arrangement direction and the second arrangement direction,
a first sequential order of the first detection element and the first compensation element is reverse to a second sequential order of the second detection element and the second compensation element,
the first detection element, the first compensation element, the second detection element, and the second compensation element are placed at apexes of a virtual square, and
the temperature sensor is placed at an intersection point of diagonal lines of a virtual square where the first detection element, the first compensation element, the second detection element, and the second compensation element are placed at four apexes of the virtual square.

2. The gas sensor according to claim 1, further comprising a heater for heating the detection chamber.

3. The gas sensor according to claim 1, further comprising:
an insulating member which reduces the thermal interference between at least two elements of the first detection element, the first compensation element, the second detection element, and the second compensation element.

4. The gas sensor according to claim 3, wherein the insulating member is preferably cross-shaped so as to reduce the thermal interference among the first detection element, the first compensation element, the second detection element, and the second compensation element.

5. The gas sensor according to claim 3, wherein the insulating member is cylindrical, and the cylindrical insulating members are provided around the first detection element and the second detection element respectively.

6. The gas sensor according to claim 5, wherein a through hole through which the detected gas passes is formed on a side wall of the cylindrical insulating member.

7. The gas sensor according to claim 6, wherein the through hole is placed at a position other than an inner position in a diagonal direction of the virtual square where the first detection element, the first compensation element, the second detection element, and the second compensation element are placed at four apexes.

* * * * *